United States Patent
Hansen

(10) Patent No.: US 7,077,131 B2
(45) Date of Patent: Jul. 18, 2006

(54) VENTILATOR WITH DUAL GAS SUPPLY

(75) Inventor: Gary Hansen, Eden Prairie, MN (US)

(73) Assignee: Mallinckrodt, Inc., St. Louis, MO (US)

( * ) Notice: Subject to any disclaimer, the term of this patent is extended or adjusted under 35 U.S.C. 154(b) by 202 days.

(21) Appl. No.: 10/246,421

(22) Filed: Sep. 19, 2002

(65) Prior Publication Data

US 2003/0015200 A1    Jan. 23, 2003

Related U.S. Application Data

(63) Continuation of application No. 09/691,139, filed on Oct. 19, 2000, now abandoned.

(51) Int. Cl.
*A61M 16/00* (2006.01)

(52) U.S. Cl. .................. 128/204.18; 128/204.21; 128/204.22; 128/205.24

(58) Field of Classification Search ........... 128/204.18, 128/204.21, 204.22, 205.18, 205.24, 203.12, 128/203.16, 205.14
See application file for complete search history.

(56) References Cited

U.S. PATENT DOCUMENTS

| | | | | |
|---|---|---|---|---|
| 4,193,406 A * | 3/1980 | Jinotti | ............... | 128/204.18 |
| 4,239,039 A | 12/1980 | Thompson | | |
| 4,391,271 A | 7/1983 | Blanco | | |
| 5,507,282 A * | 4/1996 | Younes | ............... | 128/204.21 |
| 5,592,935 A | 1/1997 | Elstran et al. | | |
| 5,687,912 A * | 11/1997 | Denyer | ............... | 239/343 |
| 5,720,280 A | 2/1998 | Elstran et al. | | |
| 5,771,928 A * | 6/1998 | Zepic et al. | ............... | 137/625.22 |
| 5,797,393 A * | 8/1998 | Kohl | ............... | 128/204.23 |
| 5,875,783 A * | 3/1999 | Kullik | ............... | 128/204.18 |
| 5,927,274 A | 7/1999 | Servidio et al. | | |
| 5,931,163 A * | 8/1999 | Stegmann et al. | ..... | 128/204.26 |
| 5,934,274 A | 8/1999 | Merrick et al. | | |
| 5,937,855 A | 8/1999 | Zdrojkowski et al. | | |
| 5,988,166 A * | 11/1999 | Hayek | ............... | 128/205.26 |
| 6,182,658 B1 * | 2/2001 | Hayek | ............... | 128/205.24 |
| 6,209,540 B1 * | 4/2001 | Sugiura et al. | ........ | 128/204.18 |
| 6,694,976 B1 * | 2/2004 | Takaki et al. | .......... | 128/204.18 |
| 6,708,690 B1 * | 3/2004 | Hete et al. | ............. | 128/204.18 |
| 6,860,265 B1 * | 3/2005 | Emerson | ............... | 128/205.12 |

FOREIGN PATENT DOCUMENTS

| | | |
|---|---|---|
| DE | 946 250 | 7/1956 |
| FR | 2 554 351 | 5/1985 |
| WO | WO 99/08738 | 2/1999 |
| WO | WO 99/47200 | 9/1999 |

\* cited by examiner

*Primary Examiner*—Glenn K. Dawson
*Assistant Examiner*—Darwin P Erezo
(74) *Attorney, Agent, or Firm*—Baker Botts L.L.P.

(57) ABSTRACT

A method of pressure regulation and a ventilator are provided. The ventilator includes a positive relative pressure gas supply, a negative relative pressure gas supply, and a diverter valve. The diverter valve includes a positive pressure port connected to the positive relative pressure gas supply, a negative pressure port connected to the negative relative pressure gas supply, and a gas supply port communicating with a gas delivery device. The ventilator preferably further includes a feedback sensor that detects a gas supply difference between a gas supply and a predetermined gas supply and generates a feedback signal that is substantially related to the gas supply difference. The ventilator preferably further includes a diverter valve actuator communicating with the diverter valve and operating the diverter valve to communicate the positive relative pressure gas supply and the negative relative pressure gas supply to the gas supply port of the diverter valve based upon the feedback signal.

25 Claims, 3 Drawing Sheets

VENTILATOR WITH DUAL GAS SUPPLY

CROSS REFERENCE OF RELATED APPLICATION

This application is a continuation of application Ser. No. 09/691,139, filed Oct. 19, 2000.

BACKGROUND OF THE INVENTION

1. Field of the Invention

The present invention relates generally to the field of medical ventilators.

2. Description of the Background Art

A medical ventilator is a device used to deliver a gas or gases to a patient. This may include air or oxygen, and may also include a variety of additive medicines or treatments. The gas is supplied to a patient via a gas delivery device such as a mask, a nasal cannula, or a tracheostomy tube. The ventilator may be used in cases where it merely assists a patient's breathing (respiratory insufficiency), or may be used in cases where the ventilator must perform breathing for the patient (respiratory failure or when the patient is under the influence of anesthesia). The ventilator may provide a constant pressure airflow, may provide a cyclic airflow, or may provide other pressure patterns. Therefore, a ventilator may need to be capable of providing a gas or gas mixture at either a steady pressure or may need to be capable of providing an output that follows a predetermined pressure or flow volume profile that corresponds to a predetermined breathing profile. The pressure profile may be a cyclic inhalation/exhalation pattern having a varying gas pressure and flow volume profiles. The pressure profile may need to be varied according to a patient's age, health, medical condition, etc.

FIG. 1 shows a prior art ventilator 100 connected to a gas delivery device 101 in the form of a mask. The prior art ventilator 100 includes a blower 105, and a pressure sensor 108. The blower may be used to achieve a gas supply pressure, and may be an electric motor turning an impeller.

In the prior art, a target gas supply pressure has typically been achieved by controlling the blower motor speed. If the pressure of the gas supply is below a predetermined pressure, the motor speed may be increased, and vice versa.

However, a variable blower speed ventilator 100 of the prior art has drawbacks. In order to keep the ventilator air circuit as light and unobtrusive as possible in order to improve wearability, the prior art ventilator 100 generally employs tubing of a small diameter. As a result, airflow resistance is increased, yielding a lower than expected pressure to the patient.

Airflow resistance is usually measured by a constant-flow pressure drop. This is the drop in pressure (usually expressed in units of centimeters of water, or cm $H_2O$) between the entrance and the exit of the tube under conditions of unvarying flow. The standard ventilator hose is typically about 22 millimeters in diameter and about 6 feet long. This creates a constant-flow pressure drop of less than 1–2 cm $H_2O$ for reasonable values of flow (such as a breathing airflow of less than 60 liters per minute). Higher peak airflow values for patients suffering from respiratory insufficiency are possible but are rare.

Recent prior art masks include short lengths of a smaller-diameter tubing (generally about 15 millimeters in diameter and about 6–18 inches long) acting as a strain relief between the bulkier air supply hose and the mask. These smaller diameter tubing segments can add 1–2 cm $H_2O$ to the pressure drop.

Clinical guidelines for regulating the air pressure to the patient vary depending on the medical use. A CPAP (continuous positive airway pressure) system may be used for nocturnal treatment of obstructive sleep apnea. In a CPAP system, the patient's airway is partially inflated by the positive pressure in order to aid breathing and sleep. Therefore, it is desirable in a CPAP system to hold the target pressure to a tolerance of about plus or minus 2 cm $H_2O$. The acceptable pressure range for other ventilator modes may extend up to plus or minus 5 cm $H_2O$. Particularly for CPAP ventilators, a more resistive patient airflow circuit (i.e., a mask and hose combined) can cause pressure regulation to the patient to vary outside an acceptable range. This creates a need for a ventilator that can more quickly compensate for rapid changes in the airflow rate.

The increased air circuit resistance may be somewhat compensated for by increasing the blower output. However, if the ventilator circuit resistance becomes too great, a blower may not be able to adjust its speed and output quickly enough to correct for pressure changes. In addition, if the blower is trying to quickly go from one pressure extreme to another, the blower direction may need to be reversed in devices of the prior art. These quick changes in motor speed and direction may cause unacceptable levels of motor heating, may require more electrical power to achieve a desired pressure, may cause much higher levels of motor wear, and still do not provide a satisfactorily fast pressure response.

There remains a need in the art for improved ventilator pressure regulation.

SUMMARY OF THE INVENTION

A ventilator is provided according to an embodiment of the invention. The ventilator comprises a positive relative pressure gas supply, a negative relative pressure gas supply, and a diverter valve. The diverter valve includes a positive pressure port connected to the positive relative pressure gas supply, a negative pressure port connected to the negative relative pressure gas supply, and a gas supply port communicating with a gas delivery device. The ventilator preferably further includes a feedback sensor that detects a gas supply difference between a gas supply and a predetermined gas supply and generates a feedback signal that is substantially related to the gas supply difference. The ventilator preferably further includes a diverter valve actuator communicating with the diverter valve and operating the diverter valve to communicate the positive relative pressure gas supply and the negative relative pressure gas supply to the gas supply port of the diverter valve based upon the feedback signal.

A method of pressure regulation for a ventilator is provided according to an embodiment of the invention. The method comprises the steps of providing a positive relative pressure gas supply, providing a negative relative pressure gas supply, and detecting a gas supply difference between a gas supply provided to a gas delivery device of the ventilator and a predetermined gas supply. The method further comprises the steps of generating a feedback signal that is substantially related to the gas supply difference, and actuating a diverter valve to communicate the positive relative pressure gas supply and the negative relative pressure gas supply to the gas delivery device in order to substantially minimize the gas supply difference.

The above and other features and advantages of the present invention will be further understood from the following description of the preferred embodiments thereof, taken in conjunction with the accompanying drawings.

DETAILED DESCRIPTION OF THE PREFERRED EMBODIMENTS

Figure 2:
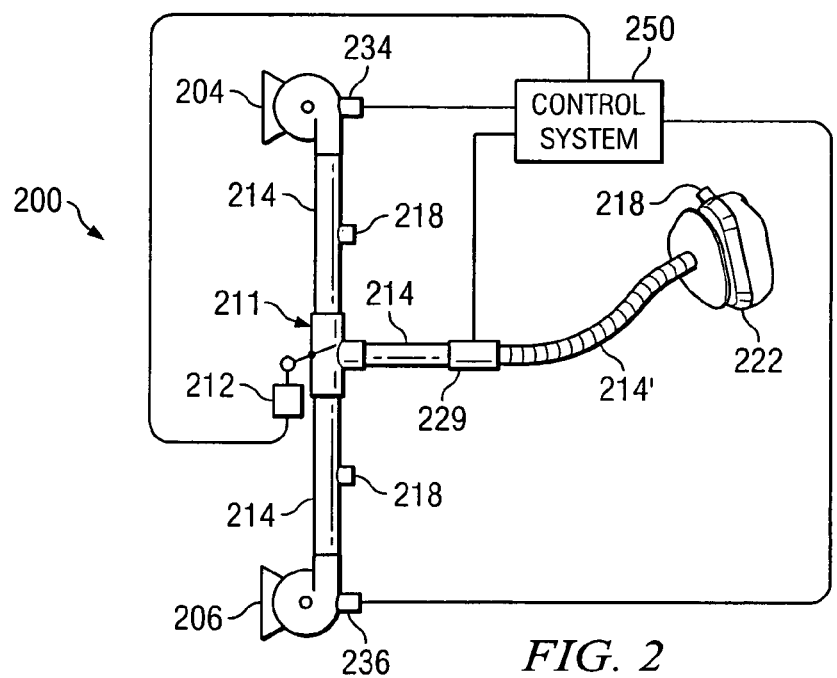
FIG. 2 shows an embodiment of a ventilator according to the invention.

FIG. 2 shows an embodiment of a ventilator 200 according to the invention. The ventilator 200 includes a positive relative pressure gas supply 204, a negative relative pressure gas supply 206, and a diverter valve 211 communicating with the positive relative pressure gas supply 204 and the negative relative pressure gas supply 206. A gas delivery device 222 in the form of a mask is also shown communicating with the diverter valve 211. By actuating the diverter valve 211 in substantial synchronization with the breathing of the patient, breathing is aided and the work required by the patient is decreased.

The positive relative pressure gas supply 204 and the negative relative pressure gas supply 206 may be motors turning associated impellers or fans (e.g., blowers). Alternatively, the gas supplies may be any form of bellows, piston, pump, fan, impeller or other device that is capable of providing a gas at an elevated relative pressure. Each blower may need to provide at least positive and negative pressures of about 35 cm $H_2O$ at the gas delivery device 222 in order to achieve a peak gas flow rate of 60 liters per minute. In a majority of patients, this will be a satisfactory flow volume. However, the ventilator 200 may preferably be capable of providing positive and negative pressures of at least 40 to 60 cm $H_2O$, or even greater. The greater the gas supply output, the greater the ability of the ventilator 200 to correct for sudden peaks in respiratory flow.

Figure 3:
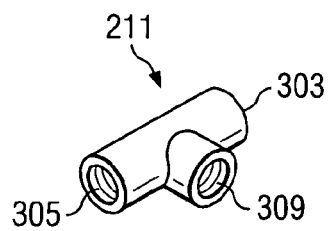
FIG. 3 shows an embodiment of a diverter valve for use with a ventilator according to the present invention.

FIG. 3 shows an embodiment of the diverter valve 211. The diverter valve 211 includes a positive pressure port 303, a negative pressure port 305, and a gas supply port 309. It should be understood that the diverter valve 211, although shown as a common tee type valve, could be a valve of any other configuration. The diverter valve 211 may be actuated to select the positive pressure port 303, the negative pressure port 305, or a ratio of both, to communicate with the gas supply port 309.

If the valve member of diverter valve 211 is constructed of a material having a relatively low mass, such as plastic, it will be capable of being rapidly actuated. Therefore, the diverter valve 211 may have a small response time, and the pressure and/or flow volume at the gas supply port 309 may be carefully regulated.

Figure 1:
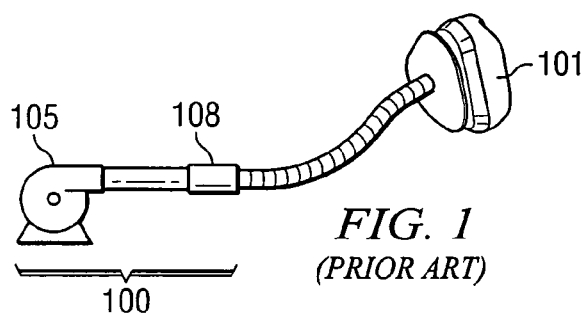
FIG. 1 shows a prior art ventilator.

The diverter valve 211 may be directly coupled to the two gas supplies 204 and 206 and to the gas delivery device 222. Alternatively, the various components may be connected by conduits 214 as shown in FIG. 1. The ventilator 200 is especially suited for use with smaller diameter tubing 214' connecting the ventilator to the gas delivery device 222 as a strain relief. Therefore, the gas supplies 204 and 206 and the diverter valve 211 may be placed at a variety of locations relative to the patient, such as formed on the gas delivery device 222, or in a backpack, belt, or chest configuration, or on a cart or table remote from the patient, etc. Ventilator 200 include one or more vent ports 218 that function to vent excess supplied gas (or exhaled carbon dioxide). The vent port 218 may be located on any of the ventilator components, such as conduit 214, or on the gas delivery device 222.

In use, the ventilator 200 may be used to maintain a predetermined gas supply to a patient. The positive relative pressure gas supply 204 creates a positive relative gas pressure for the diverter valve 211, while the negative relative pressure gas supply 206 creates a negative relative gas pressure for the diverter valve 211. The diverter valve 211 may be used to communicate the positive relative pressure gas supply 204 and the negative relative pressure gas supply 206 to the gas delivery device 222. The predetermined gas supply pressure achieved through use of the diverter valve 211 may therefore be a predetermined pressure and/or flow volume profile that substantially corresponds to a patient's breathing.

The resulting gas pressure at the gas delivery device 222 may therefore be any pressure in the negative-positive relative pressure range. This enables a quick and accurate control of the gas pressure supplied to the gas delivery device 222. In this manner, using the two gas supplies 204 and 206, pressure regulation is achieved and the patient may be aided in breathing without having to change the speed of an associated blower. This extends motor life, creates less noise, and allows lower motor running temperatures. Alternatively, the two gas supplies 204 and 206 may be used to achieve a predetermined flow volume, instead of a predetermined pressure. The end result in both cases is a delivery to the patient of a predetermined gas supply to aid in breathing. Although the pressure is commonly referred to in this description, it should be understood that the two gas supplies 204 and 206 and the diverter valve 211 may be operated according to either the pressure or the flow volume in the ventilator.

In a first diverter valve embodiment, the diverter valve 211 may be capable of a continuous range of movement. Therefore, gas supply regulation may be achieved by positioning the diverter valve 211 anywhere in between the two selections and the two pressure extremes. In this manner, for example, the pressure at the gas supply port 309 may be the positive relative pressure, the negative relative pressure, or some level in between. At a time period between inhalations and exhalations, for example, the diverter valve 211 may be halfway open, and as a result there may be airflow only from the positive relative pressure gas supply to the negative relative pressure gas supply, and essentially no airflow into the gas delivery device 222. At the start of inhalation or exhalation, however, the diverter valve 211 may be near one of the extremes of travel in order to provide a desired pressure or flow volume.

In another embodiment, the diverter valve 211 may be an either-or valve, where either the positive pressure port 303 is selected or the negative pressure port 305 is selected, but not both. A predetermined pressure may be maintained in this embodiment by periodically actuating the diverter valve 211 between either pressure supply port. The actuation duty cycle may be varied to achieve a predetermined pressure (or pressure profile) at any level between the positive pressure gas supply 204 or the negative relative pressure gas supply 206 (e.g., by fluttering the diverter valve 211).

Also shown in FIG. 2 are the feedback and control components that determine the pressure in the ventilator and actuate the diverter valve 211 in response. The ventilator 200 therefore includes a control system 250 and a feedback sensor of some type. The control system 250 is capable of actuating the diverter valve 211 by sending an appropriate control signal to the actuator 212. In order to actuate the diverter valve 211, the control system 250 must be able to determine a switching time. The actuation may be done in response to a feedback signal generated by one or more feedback sensors. The feedback sensor may be a pressure or flow volume sensor 229 positioned on or between the diverter valve 211 and the mask 222. Alternatively, or in addition to sensor 229, one or more motor speed sensors 234 and 236, such as an electrical load sensor, an optical rotational speed sensor, a magnetic rotational speed sensor, a mechanical rotational speed sensor or the like, may be associated with corresponding gas supplies 204 and 206.

The control system 250 may be any type of analog or digital electronic feedback control, such as a proportional controller, a proportional integral derivative (PID) controller, or a computer processor programmed to implement one or more predetermined breathing profiles. The control system 250 may function to assist patients with respiratory insufficiency or may perform ventilation for patients with respiratory failure. Depending on the type of ventilation required, different breathing patterns and pressure levels may be needed. In addition, the ventilator 200 may accommodate patients of different ages and in various states of health. Various ventilation pressure or flow volume profiles may be programmed into the control system 250 and recalled.

By varying the gas supply at the gas delivery device 222 based on a detected gas supply level, the ventilator 200 may provide adequate ventilation but yet accommodate different lung capacities, without the need for calibration.

In a first feedback sensor embodiment, the ventilator 200 includes a sensor 229 in the form of a pressure sensor positioned on or between the diverter valve 211 and the gas delivery device 222. The pressure sensor 229 may generate a feedback signal that is substantially related to the gas supply pressure. The feedback signal may be compared to a predetermined or desired pressure or pressure profile in order to generate a pressure difference. The pressure difference may be used to actuate the diverter valve 211 according to any known feedback and control algorithm.

Figure 4:
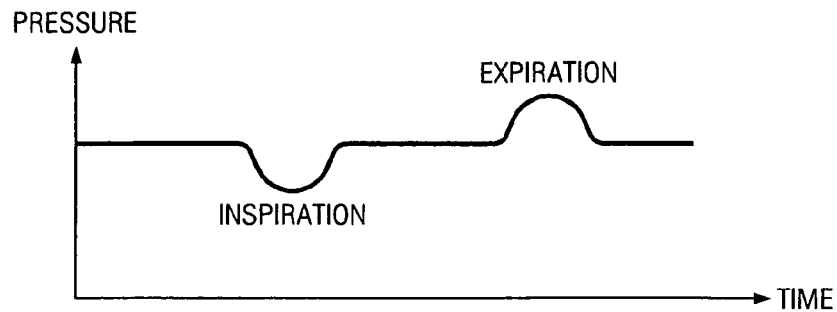
FIG. 4 is a pressure graph of a representative pressure profile during a typical breathing cycle.

FIG. 4 is a pressure graph of a representative pressure profile during a typical breathing cycle. This may be the pressure at the gas delivery device 222.

In a second embodiment, the feedback sensor 229 is a flow volume sensor positioned on or between the diverter valve 211 and the gas delivery device 222. The flow volume sensor 229 measures a flow volume of gas. The flow volume may be used to signify pressure changes and determine when the patient is inhaling or exhaling (see FIG. 5 and accompanying discussion below). The flow volume sensor 229 may generate a feedback signal that is substantially related to the gas supply flow volume. The feedback signal may be compared to a predetermined or desired flow volume or flow volume profile in order to generate a flow volume difference. The flow volume difference may be used to actuate the diverter valve 211 according to any known feedback and control algorithm.

Figure 5:
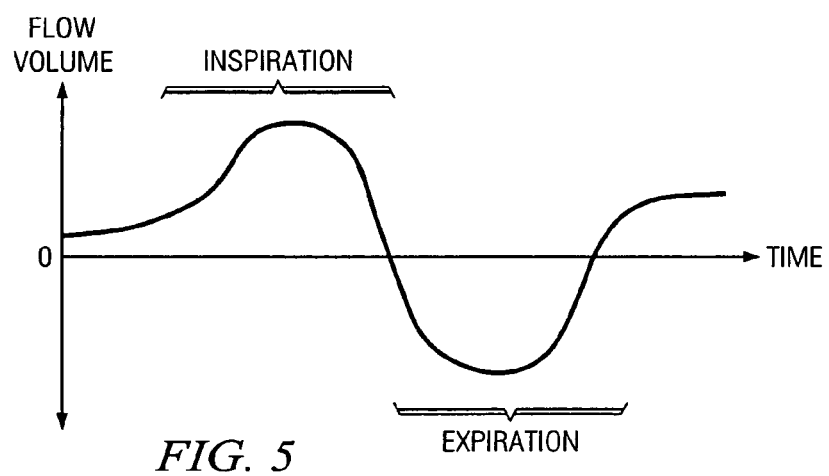
FIG. 5 is a flow volume graph of a representative flow volume during a typical breathing cycle.

FIG. 5 is a flow volume graph of a representative flow volume during a typical breathing cycle. This may be the flow volume at the gas delivery device 222. As can be seen from the graph, the gas flow volume varies regularly with the patient's breathing. This figure shows that the changes in flow volume correspond to the changes in pressure, and illustrates why the flow volume measurement is substantially analogous to the pressure measurement. Therefore, the flow volume measurement may be used to control the diverter valve 211.

In a third embodiment, one or more motor speed sensors 234 and 236 are used to control the diverter valve 211. In the two motor speed sensors embodiment, for example, the point in time when the motor speed of the positive relative pressure gas supply 204 drops, patient inhalation has stopped and exhalation has begun. As the positive pressure continues to be supplied, the pressure in the ventilator increases when the patient stops inhaling (i.e., an airflow backup occurs). This increase in pressure will cause the motor of the positive relative pressure gas supply 204 to slow down. Therefore, the control system 250 may now control the actuator 212 and move the diverter valve 211 to select the negative pressure port 305 and the negative relative pressure gas supply 206, or select a greater opening percentage for the negative pressure port 305.

Conversely, when the motor speed of the negative relative pressure gas supply 206 drops, as detected by the motor speed sensor 236, exhalation has stopped and inhalation has begun. The control system 250 may now control the actuator 212 and move the diverter valve 211 to select the positive pressure port 303 and the positive relative pressure gas supply 204, or select a greater opening percentage for the positive pressure port 303.

Figure 6:
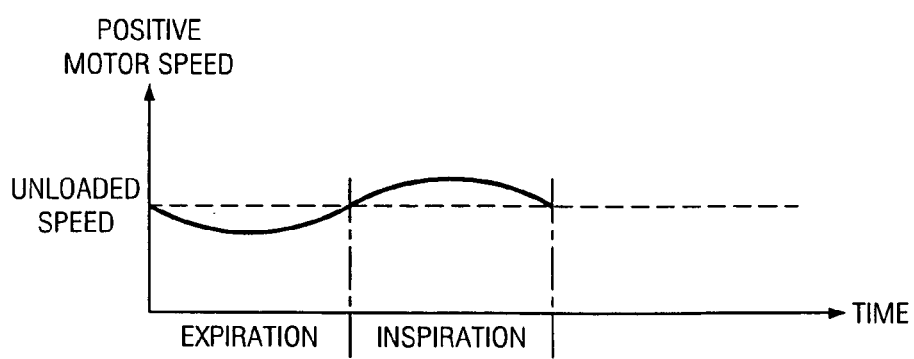
FIG. 6 is a motor speed graph of a representative positive gas supply motor speed.

FIG. 6 is a motor speed graph of a representative positive gas supply motor speed. The graph shows how the motor speed may be affected by inspiration and expiration and shows how the motor speed may therefore be detected and used to control the diverter valve 211.

Figure 7:
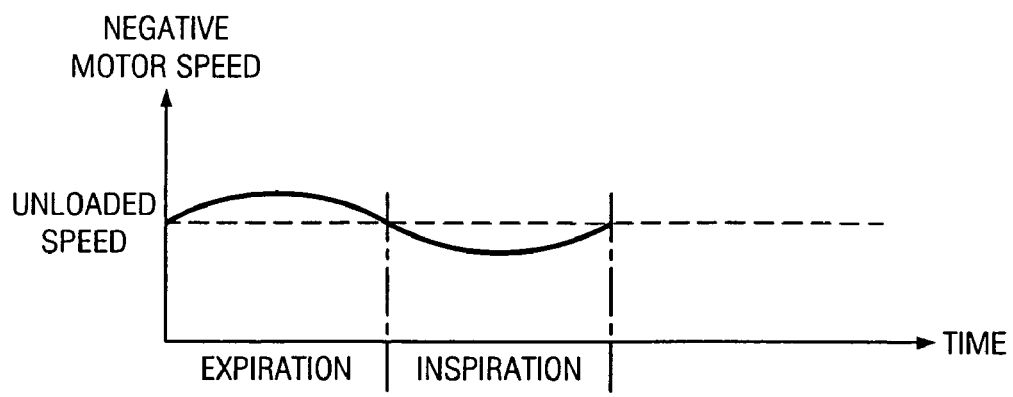
FIG. 7 is a motor speed graph of a representative negative gas supply motor speed.

FIG. 7 is a motor speed graph of a representative negative gas supply motor speed. The diverter valve 211 may be actuated using the speed of one or both motors. In a one motor speed sensor embodiment, a motor speed sensor at the positive relative pressure gas supply 204 would see a substantial increase in pressure at the start of a patient exhalation cycle, and would see a substantial drop in pressure at the start of a patient inhalation cycle.

In comparison, in a two speed sensor embodiment, the positive motor speed sensor 234 may be used to determine the end of inhalation and the start of exhalation, while the negative motor speed sensor 236 may be used to determine the end of exhalation and the start of inhalation. By using the speed of both motors, the inspiration and expiration cycles may be detected with more precision. In addition, the redundancy of two speed sensors may provide the ventilator pressure regulator 200 with an extra level of reliability.

Figure 8:
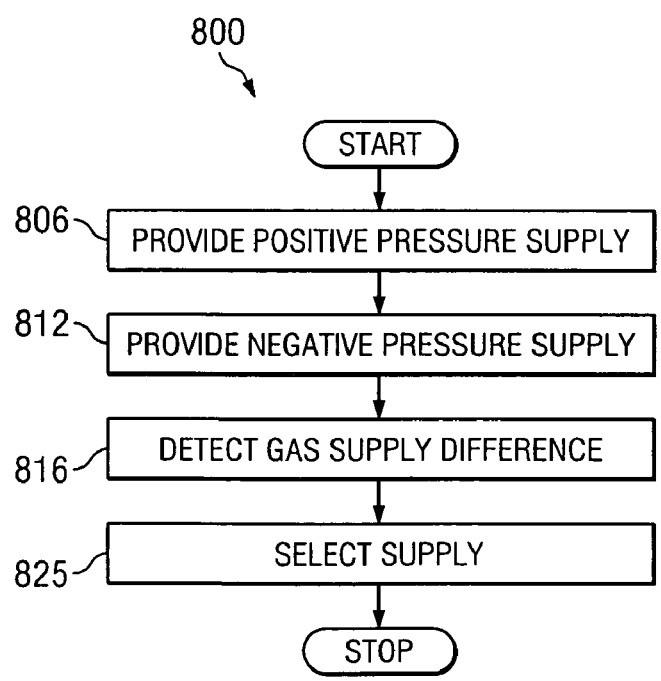
FIG. 8 is a flowchart of a ventilator pressure regulation method embodiment according to the invention.

FIG. 8 is a flowchart 800 of a ventilator pressure regulation method embodiment according to the invention. In step 806, a positive relative pressure gas supply is provided. The positive relative pressure gas supply may be any form of bellows, piston, pump, fan, impeller or other device that is capable of providing a gas at a positive relative pressure (i.e., a gas at a pressure greater than the ambient air pressure).

In step 812, a negative relative pressure gas supply is provided. The negative relative pressure gas supply may likewise be any form of bellows, piston, pump, fan, impeller or other device that is capable of providing a gas at a negative relative pressure.

In step 816, a pressure difference between a gas supply and a predetermined or desired gas supply is detected. The gas supply may be detected using the pressure, flow volume, or motor speed, and is a determination of the gas being supplied to a gas delivery device of the ventilator. The pressure difference may be detected by measuring the gas supply pressure, by measuring a gas supply flow volume, blower motor speeds, etc., as previously discussed.

In step 825, the positive relative pressure gas supply 204 and the negative relative pressure gas supply 206 are selected to be communicated to the gas delivery device 222. As previously described, the selection may be selecting one of the two gas supplies, or the selection device may be at some position in between wherein both the positive supply 204 and the negative supply 206 are partially communicating with the gas delivery device 222. In this manner, a predetermined gas supply pressure to the gas delivery device 222 may be substantially achieved.

Although the ventilator 200 as described above is discussed in the context of a pressure regulator for respiratory therapy, it should be understood that the invention may enjoy other uses. This may include use as a breathing simulator, for example, that could be used to develop and test further ventilators of associated ventilation devices and control or monitoring routines.

While the invention has been described in detail above, the invention is not intended to be limited to the specific embodiments as described. It is evident that those skilled in the art may now make numerous uses and modifications of and departures from the specific embodiments described herein without departing from the inventive concepts.

What is claimed is:

1. A ventilator comprising:
   a positive relative pressure gas supply;
   a negative relative pressure gas supply;
   a gas delivery device for delivering gas to a patient;
   a diverter valve including a positive pressure port connected to said positive relative pressure gas supply, a negative pressure port connected to said negative relative pressure gas supply, and a gas supply port for communicating with said gas delivery device, wherein a gas supply from at least one of said positive relative pressure gas supply and said negative relative pressure gas supply is delivered to said gas delivery device for delivery of said gas to said patient, via said diverter valve:
   a feedback sensor that detects a gas supply difference between said gas supply and a predetermined gas supply and generates a feedback signal that is substantially related to said gas supply difference; and
   a diverter valve actuator communicating with said diverter valve and operating said diverter valve to communicate said positive relative pressure gas supply and said negative relative pressure gas supply to said gas supply port of said diverter valve based upon said feedback signal.

2. The ventilator of claim 1, wherein said diverter valve is configured to allow selection of a mixture ratio of said positive relative pressure gas supply and said negative relative pressure gas supply for communicating with said gas supply port.

3. The ventilator of claim 1, further comprising a control system that receives said feedback signal and commands said diverter valve actuator.

4. The ventilator of claim 1, further comprising a control system that receives said feedback signal and commands said diverter valve actuator and wherein said control system commands said diverter valve actuator to substantially achieve a predetermined breathing profile.

5. The ventilator of claim 1, wherein said ventilator further comprises a vent port.

6. The ventilator of claim 1, wherein said diverter valve actuator is a linear actuator capable of positioning said diverter valve.

7. The ventilator of claim 1, wherein said feedback sensor comprises a pressure sensor that measures a pressure of gas being supplied to said gas delivery device.

8. The ventilator of claim 1, wherein said feedback sensor comprises a flow volume sensor that measures a volume of gas being supplied to said gas delivery device.

9. The ventilator of claim 1, wherein said positive relative pressure gas supply and said negative relative pressure gas supply comprise blowers and motors and wherein said motors run at a substantially constant speed.

10. The ventilator of claim 1, wherein said positive relative pressure gas supply and said negative relative pressure gas supply comprise blowers and motors and wherein said feedback sensor is an electrical load sensor that measures an electrical load of said blowers and motors.

11. The ventilator of claim 1, wherein said positive relative pressure gas supply and said negative relative pressure gas supply comprise blowers and motors and wherein said feedback sensor is an optical rotational speed sensor that measures a motor speed.

12. The ventilator of claim 1, wherein said positive relative pressure gas supply and said negative relative pressure gas supply comprise blowers and motors and wherein said feedback sensor is a magnetic rotational speed sensor that measures a motor speed.

13. The ventilator of claim 1, wherein said positive relative pressure gas supply and said negative relative pressure gas supply comprise blowers and motors and wherein said feedback sensor is mechanical rotational speed sensor that measures a motor speed.

14. The ventilator of claim 1, wherein said diverter valve is configured to allow selection between said positive pressure port and said negative pressure port for communicating with said gas supply port.

15. A method of pressure regulation for a ventilator, comprising the steps of:
    providing a positive relative pressure gas supply;
    providing a negative relative pressure gas supply;
    providing a gas delivery device for delivering gas to a patient;
    detecting a gas supply difference between a gas supply provided to said gas delivery device of said ventilator and a predetermined gas supply;
    generating a feedback signal that is substantially related to said gas supply difference;
    actuating a diverter valve to communicate said positive relative pressure gas supply and said negative relative pressure gas supply to said gas delivery device in order to substantially minimize said gas supply difference; and
    delivering gas through said diverter valve to said gas delivery device for delivering said gas to said patient.

16. The method of claim 15, wherein said detecting step comprises measuring a flow volume of said gas supply.

17. The method of claim 15, wherein said detecting step comprises measuring motor speeds of motors and impellers used to generate said positive relative pressure gas supply and said negative relative pressure gas supply.

18. The method of claim 15, wherein said detecting step comprises measuring electrical loads on motors and impellers used to generate said positive relative pressure gas supply and said negative relative pressure gas supply.

19. The method of claim 15, wherein said actuating step further comprises actuating a valve to select a mixture ratio of said positive relative pressure gas supply to said negative relative pressure gas supply.

20. The method of claim 15, wherein said method cycles said diverter valve to achieve a substantially predetermined flow volume.

21. The method of claim 15, wherein said method cycles said diverter valve to achieve a substantially predetermined pressure.

22. The method of claim 15, wherein said detecting step comprises measuring a pressure of said gas supply.

23. The method of claim 15, wherein said actuating step further comprises actuating a valve to select only said negative relative pressure gas supply.

24. The method of claim 15, wherein said actuating step further comprises actuating a valve to select only said positive relative pressure gas supply.

25. A ventilator, comprising:
  a positive relative pressure gas supply operable to supply positive relative pressure; a negative relative pressure gas supply operable to supply negative relative pressure; a gas delivery device for delivering gas to a patient; and
  a diverter valve including a positive pressure port connected to said positive relative pressure gas supply, a negative pressure port connected to said negative relative pressure gas supply, and a gas supply port for communicating with said gas delivery device;
  wherein a gas supply from at least one of said positive relative pressure gas supply and said negative relative pressure gas supply is delivered to said gas delivery device for delivery of said gas to said patient via said diverter valve;
  wherein said diverter valve is configured to allow selection of a mixture ratio of said positive relative pressure gas supply and said negative relative pressure gas supply for communicating with said gas supply port;
  wherein a feedback sensor that detects a gas supply difference between said gas supply and a predetermined gas supply generates a feedback signal that is substantially related to said gas supply difference; and
  wherein a diverter valve actuator communicating with said diverter valve and operating said diverter valve communicates said positive relative pressure gas supply and said negative relative pressure gas supply to said gas supply port of said diverter valve based upon said feedback signal.

* * * * *